US012349863B2

(12) United States Patent
Honegger

(10) Patent No.: US 12,349,863 B2
(45) Date of Patent: Jul. 8, 2025

(54) DATA PROCESSING DEVICE AND COMPUTER-IMPLEMENTED METHOD COMBINING TWO IMAGES AND AN OVERLAY COLOR USING A UNIFORM COLOR SPACE

(71) Applicant: Leica Instruments (Singapore) Pte. Ltd., Singapore (SG)

(72) Inventor: Marc Honegger, Singapore (SG)

(73) Assignee: LEICA INSTRUMENTS (SINGAPORE) PTE. LTD., Singapore (SG)

( * ) Notice: Subject to any disclaimer, the term of this patent is extended or adjusted under 35 U.S.C. 154(b) by 0 days.

(21) Appl. No.: 18/864,558

(22) PCT Filed: May 15, 2023

(86) PCT No.: PCT/EP2023/062882
§ 371 (c)(1),
(2) Date: Nov. 11, 2024

(87) PCT Pub. No.: WO2023/218084
PCT Pub. Date: Nov. 16, 2023

(65) Prior Publication Data
US 2025/0169677 A1     May 29, 2025

(30) Foreign Application Priority Data
May 13, 2022   (EP) .................................... 22173315

(51) Int. Cl.
*A61B 1/00*   (2006.01)
*G06T 7/00*   (2017.01)

(52) U.S. Cl.
CPC .............. *A61B 1/0005* (2013.01); *G06T 7/97* (2017.01); *G06T 2207/10068* (2013.01); *G06T 2207/20221* (2013.01)

(58) Field of Classification Search
None
See application file for complete search history.

(56) References Cited

U.S. PATENT DOCUMENTS

2003/0013937 A1*   1/2003   Tsujita ............... A61B 1/00186
                                                              600/109
2017/0258330 A1   9/2017   Tsumatori
(Continued)

FOREIGN PATENT DOCUMENTS

EP      3037030 A1   6/2016
EP      3205254 A1   8/2017

*Primary Examiner* — John P Leubecker
(74) *Attorney, Agent, or Firm* — LEYDIG, VOIT & MAYER, LTD.

(57) ABSTRACT

A data processing device is configured to retrieve background color coordinates of a background color, retrieve overlay color coordinates of an overlay color, retrieve a light intensity value, compute a luminance line extending from the overlay color coordinates to an end point, determine a first point on the luminance line based on a difference between a maximum luminance value and a luminance of the background color coordinates and a difference between the luminance and a minimum luminance, compute an overlay color line that extends straight from the background color coordinates to the first point, and determine a second point on the overlay color line based on a difference between a maximum light intensity value and the light intensity value and a difference between the light intensity value and a minimum light intensity value, and output color coordinates of the second point as an output color of an output pixel.

15 Claims, 4 Drawing Sheets

(56) References Cited

U.S. PATENT DOCUMENTS

| | | | |
|---|---|---|---|
| 2020/0150041 A1* | 5/2020 | Harootunian | G01N 21/6456 |
| 2020/0170492 A1* | 6/2020 | Kuramoto | A61B 5/489 |
| 2020/0204776 A1* | 6/2020 | Themelis | A61B 90/30 |
| 2022/0211259 A1* | 7/2022 | Kuramoto | A61B 1/000094 |
| 2023/0248209 A1* | 8/2023 | Tanigami | A61B 1/05 |
| | | | 600/109 |

* cited by examiner

DATA PROCESSING DEVICE AND COMPUTER-IMPLEMENTED METHOD COMBINING TWO IMAGES AND AN OVERLAY COLOR USING A UNIFORM COLOR SPACE

CROSS REFERENCE TO RELATED APPLICATIONS

This application is a U.S. National Phase application under 35 U.S.C. § 371 of International Application No. PCT/EP2023/062882, filed on May 15, 2023, and claims benefit to European Patent Application No. 22173315.7, filed on May 13, 2022. The International Application was published in English on Nov. 16, 2023 as WO 2023/218084 A1 under PCT Article 21(2).

FIELD

Embodiments of the present invention relate to a data processing device and to a computer-implemented method for computing an output color of an output pixel in an output color image by mixing a background color of a first pixel in a background color image with an overlay color depending on a light intensity value of a second pixel in a second image.

BACKGROUND

In some applications it is desired to mix two images and to highlight in the resulting image the information which was contained in one of the two images in a predetermined overlay color, which may be, for example, a false color or a pseudocolor.

One such application is in fluorescence imaging, as e.g. used in medical observation devices such as microscopes and endoscopes. Here, a background color image may be recorded to provide a reflectance image of an object. The reflectance image may, for example, be used to show the anatomy of the region where surgery takes place. The object may contain or may be artificially provided with one or more fluorophores which emit fluorescence upon excitation. These fluorophores may be used to highlight regions of interest. For example, some fluorophores may accumulate in tumours so that tumours can be more easily detected during surgery by their fluorescence. Other fluorophores may be used to highlight blood vessels. A fluorescence image may be recorded as the second image using only wavelengths that are contained in the fluorescence emission spectrum of the at least one fluorophore. In such a configuration, the background information and the fluorescence information are contained in two different images. To bring this information together in a single image, the background image and the fluorescence image are combined (or "mixed"). This allows a surgeon or other medical personnel to identify the fluorescing region within the background image. It is desired that the fluorescing region of interest is immediately recognizable. Therefore, the fluorescence is assigned an overlay color which may correspond to the natural color of the fluorescence or to a pseudocolor.

Mixing the background color image with the second image and the overlay color in a way that all information is visually maintained and no artifacts are introduced is a challenging process. As the intensity of fluorescence is usually much lower than the intensity of the reflected light, special care needs to be taken to ensure that the combination of the fluorescence image and the background image keeps as much information from both images as possible.

SUMMARY

Embodiments of the present invention provide a data processing device for computing an output color of an output pixel in an output color image by mixing a background color of a first pixel in a background color image with an overlay color depending on a light intensity value of a second pixel in a second image. The data processing device is configured to perform operations comprising: retrieve background color coordinates of the background color in a uniform color space, the background color having a predetermined maximum luminance value and a predetermined minimum luminance value in the uniform color space, retrieve overlay color coordinates of the overlay color in the uniform color space, and retrieve the light intensity value. The light intensity value is in a range extending from and including a predetermined minimum light intensity value to and including a predetermined maximum light intensity value. The data processing device is further configured to compute a luminance line in the uniform color space. The luminance line extends from the overlay color coordinates to an end point. A luminance at the end point is lower than a luminance at the overlay color coordinates. The luminance line extends along points having a chroma of the overlay color coordinates. The data processing device is further configured to determine a first point on the luminance line. A ratio of a difference between the predetermined maximum luminance value and a luminance of the background color coordinates and a difference between the luminance of the background color coordinates and the predetermined minimum luminance value corresponds to a ratio of a length of the luminance line between the first point and the overlay color coordinates and a length of the luminance line between the end point and the first point. The data processing device is further configured to compute an overlay color line that extends straight from the background color coordinates to the first point, and determine a second point on the overlay color line. A ratio of a difference between the predetermined maximum light intensity value and the light intensity value and a difference between the light intensity value and the predetermined minimum light intensity value corresponds to a ratio of a length of the overlay color line between the second point and the first point and a length of the overlay color line between the background color coordinates and the second point. The data processing device is further configured to output color coordinates of the second point in the uniform color space as the output color of the output pixel.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
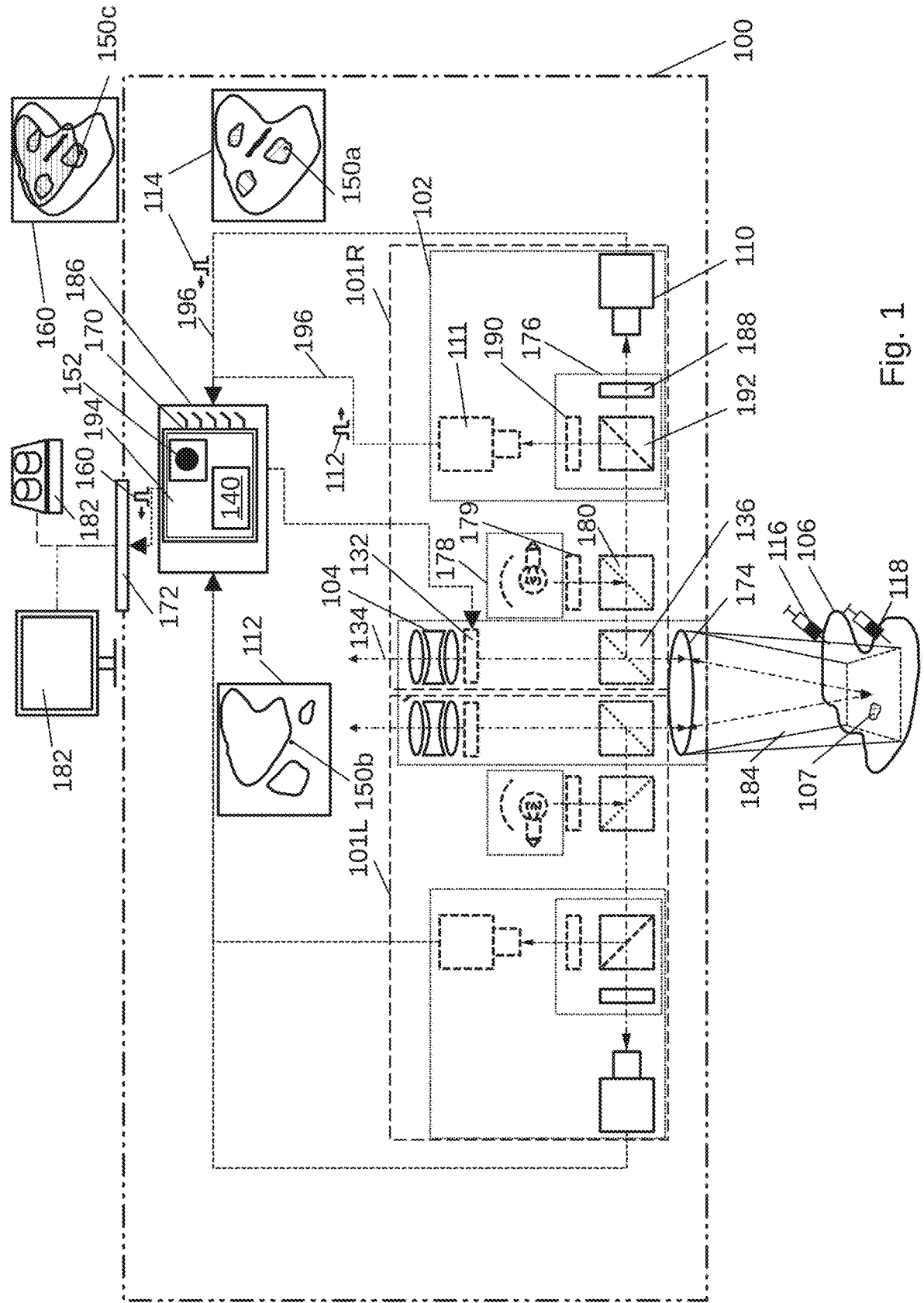
FIG. 1 shows a schematic representation of an embodiment of a medical fluorescence observation device.

Embodiments of the invention according to some embodiments not limited to the combination of images where the background image is a reflectance image and the second image is a fluorescence image. There are situations where two reflectance images of the same object, but recorded using different spectra or wavelengths, need to be mixed. For example, other applications may require that a thermal, microwave or radar image is combined with a background image.

In all these situations, it is desired that the mixing of the background image and the second image using the overlay color preserves as much information as possible.

According to some embodiments, a data processing device is configured to retrieve background color coordinates of the background color in a uniform color space, the background color having a predetermined maximum luminance value and a predetermined minimum luminance value in the uniform color space; retrieve overlay color coordinates of the overlay color in the uniform color space; retrieve the light intensity value, the light intensity value being in a range extending from and including a predetermined maximum light intensity value and extending to and including a predetermined maximum light intensity value; compute a luminance line in the uniform color space, the luminance line extending from the overlay color coordinates to an end point, the luminance at the end point being lower than the luminance at the overlay color coordinates, the luminance line extending along points having the chroma of the overlay color coordinates; determine a first point on the luminance line, wherein the ratio of the difference between the predetermined maximum luminance value and the luminance of the background color coordinates and the difference between the luminance of the background color coordinates and the predetermined minimum luminance value corresponds to the ratio of the length of the luminance line between the first point and the overlay color coordinates and the length of the luminance line between the end point and the first point; compute an overlay color line which extends straight from the background color coordinates to the first point; determine a second point on the overlay color line, wherein the ratio of the difference between the predetermined maximum light intensity value and the light intensity value and the difference between the light intensity value and the predetermined minimum light intensity value corresponds to the ratio of the length of the overlay color line between the second point and the first point and the length of the overlay color line between the background color coordinates and the second point; and output the color coordinates of the second point in the uniform color space as the output color of the output pixel.

The above need is also addressed by a computer-implemented method which comprises the following steps: retrieving background color coordinates of the background color in a uniform color space, the uniform color space having a predetermined maximum luminance value and a predetermined minimum luminance value; retrieving overlay color coordinates of the overlay color in the uniform color space; retrieving the light intensity value, the light intensity value being in a range extending from and including a minimum light intensity value and extending to and including a maximum light intensity value; computing a luminance line in the uniform color space, the luminance line extending from the overlay color coordinates to an end point, the luminance at the end point being lower than the luminance at the overlay color coordinates, the luminance line extending along points having the chroma of the overlay color coordinates; determining a first point on the luminance line, wherein the ratio of the difference between the predetermined maximum luminance value and the luminance of the background color coordinates and the difference between the luminance of the background color coordinates and the predetermined minimum luminance value corresponds to the ratio of the length of the luminance line between the first point and the overlay color coordinates and the length of the luminance line between the end point and first point; computing an overlay color line which extends straight from the background color coordinates to the first point; determining a second point on the overlay color line, wherein the ratio of the difference between the maximum light intensity value and the light intensity value and the difference between the light intensity value and the minimum light intensity value corresponds to the ratio of the length of the overlay color line between the second point and the first point and the length of the overlay color line between the background color coordinates and the second point; and outputting the color coordinates of the second point in the uniform color space as the output color.

Using the above pixel-wise combination of the background color image, the second image and the overlay color solves several problems associated with conventional mixing processes. First, the color transitions are better adapted to the physics of human visual perception; the color transitions appear more natural. Second, oversaturation is prevented. Third, non-linear dependencies, which may lead to unforeseen results, are avoided.

The (perceptually) uniform color space is a color space in which a geometrical distance corresponds to the perceived color difference. The uniform color space may be a color space from the group containing a tristimulus color space such as CIE 1931 color space, and color spaces derived from CIELUV, CIELAB, HSLuv, IPT color space and OKLab.

The predetermined maximum luminance value and the predetermined minimum luminance value may depend on the chroma of the background color. For a given chroma, the maximum luminance value and the minimum luminance value are determined by the color space or, if a display device is considered, the gamut of this display device. In this text, the terms color and color coordinates are used synonymously. A color is represented by color space coordinates. The color space coordinates for the same color are different in different color spaces.

The maximum light intensity value and the minimum light intensity value may be determined by the color space or the gamut of the predetermined displace device, in particular for a neutral color. For example, the maximum light intensity value may correspond to white and the minimum light intensity value may correspond to black in the uniform color space or the gamut. The maximum light intensity value and the minimum light intensity value may also be determined by the camera that recorded the second image.

The term "outputting" comprises both sending the outputted data and allowing access to the outputted data, e.g. by allowing access to a memory in which the color coordinates of the second point are stored.

The terms "data processing device", "image processor" or "processor" are used synonymously in this text.

In the following, further features are explained. Each of the following features is advantageous on its own and may be independently combined with any other of the following features.

Each of the following features may be used independently for improving the data processing device or the computer-implemented method, even if the respective feature is only mentioned in the context of the data processing device or only in the context of the computer-implemented method. More specifically, the data processing device may be configured to execute each of the method steps that are described below, even if the data processing device is not specifically mentioned in connection with this method step.

According to one aspect, the ratio of luminance at the end point of the luminance line to the luminance of the overlay color may be constant for a plurality or all pixels in the background image, the second image and/or the output image. For example, the ratio may be set at a value between 0.1 and 0.4, meaning that the luminance at the end point is between 10% and 40% of the luminance of the overlay color. The ratio may be adjusted by a user and/or be stored in a memory of the data processing device.

The ratio of the luminance of the overlay color coordinates and the luminance at the end point of the luminance line may, in particular, be independent of the background color coordinates of the first pixel and/or the light intensity value of the second pixel. Preferably, the ratio is constant for all pixels in the background color image and the second image.

In one embodiment, the end point of the luminance line may be located within the gamut of the predetermined display device. This configuration ensures that the end point can be properly displayed on the predetermined display device. The predetermined display may be an external monitor such as a VR device, an LED or OLED screen or projector, or a monitor that is integrated in an eyepiece of the medical observation device.

For example, if the end point which as been computed using the predetermined ratio of the luminance of the overlay color coordinates falls outside the gamut, the end point may be automatically shifted along the luminance line to a position where the luminance line crosses the limits of the gamut.

According to another embodiment, the luminance line may be a straight line or a curved line in the uniform color space. If one dimension of the uniform color space is luminance, the luminance line may extend in parallel to this dimension.

If the overlay color coordinates are provided in a non-uniform color space, they should be transformed to the uniform color space before or while being retrieved. The data processing device may be configured to perform such a color space transformation. The functions for color space transformations may be standardized or determined experimentally.

The non-uniform color space may, for example, be a RGB color space such as RGB, sRGB, AdobeRGB, Adobe White Gamut RGB, Rec. 2100, DCI-P3, Rec. 2020, Rec. 709, Rec. 601 or ACES. Other non-uniform color spaces are, for example, HSV, HSL, YUV and YCbCr as well as derivatives thereof.

If the background color coordinates are in a non-uniform color space, it is preferred that they are transformed to the uniform color space before or while being retrieved. The data processing device may be configured to perform such a transformation.

The color coordinates of the second point on the overlay color line may be transformed from the uniform color space to a non-uniform color space before output. This may be preferred if the display device is not capable of handling the color coordinates of the uniform color space.

The background color image and the second image may, in one embodiment, be registered images. In registered images, the orientation, form, size and location of patterns coincide. The registered images are congruent and thus comprise corresponding pixels. Corresponding pixels, i.e. pixels which represent the same area of a pattern, have the same location in both the background color image and the second image if the two are registered. This does not necessarily imply that both images have the same pixel resolution. One pixel in one image may correspond to a plurality of pixels in the other image. For example, a first pixel may correspond to a plurality of second pixels or a second pixel may correspond to a plurality of first pixels, if one of the images has a higher resolution. Preferably, however, the background color image and the second image have the same format and the same amount of pixels. For example, both images may be 1 k, 2 k, 4 k or 8 k images.

The registration may be carried out by the computer-implemented method and/or the data processing device.

It is further preferred that a location of the output pixel corresponds to the location of at least one of the first pixel and the second pixel. The output color image may have the same format and number of pixels as any of the background color image and the second image.

Retrieving the background color coordinates may comprise retrieving the first pixel which comprises the background color coordinates. Retrieving the first pixel may, in turn, comprise retrieving the background color image. For example, the background color image may be loaded in its entirety or on a pixel-by-pixel base into a memory of the data processing device.

Retrieving the light intensity value may comprise retrieving the second pixel, wherein the second pixel comprises the light intensity value. Further, retrieving the second pixel may comprise retrieving the second image. For example, the second image may be loaded in its entirety or on a pixel-by-pixel base into a memory of the data processing device.

The second image may, in one embodiment, be one of a greyscale image and a color image. If the second image is a greyscale image, the greyscale value may already correspond to the light intensity value. This value can then be used for determining the location of the second point on the overlay color line. The second image may be recorded by a greyscale camera or a color camera.

If the second image is a color image, retrieving the light intensity value may comprise computing the light intensity value from the color coordinates of the second pixel. This computation may be part of retrieving the light intensity value. The computation of the light intensity value can be done in any color space, i.e. in a non-uniform color space or in the uniform color space, using a standardized function or using an experimentally-determined function.

The computation of the luminance line and the overlay color line as described above, is preferably repeated for a plurality or all pixels in the background color image and the second image. The overlay color coordinates are preferably independent of the first and the second pixel. The overlay color coordinates may, for example, be a constant value that can be changed by a user.

As initially explained, one field of application of the data processing device and/or the computer-implemented method may be fluorescence imaging where the background color image may be recorded in a first imaged spectrum and may comprise a plurality of first pixels. For example, the background color image may be a digital white-light color image. The second image may be recorded in a second imaged spectrum and may comprise a plurality of second pixels also. The second imaged spectrum may overlap a fluorescence emission spectrum of at least one fluorophore. Thus, the fluorescence of the at least one fluorophore may be recorded in the second imaged spectrum. For example, the second image may be a digital fluorescence-light image. Further, the second imaged spectrum may be different from the first imaged spectrum. For example, the first imaged spectrum and the second imaged spectrum may be complementary. The first and second imaged spectrum may comprise both a plurality of stop bands and passbands. A stop band in the first imaged spectrum may correspond to a passband in the second imaged spectrum and a passband in the first imaged spectrum may correspond to a stop band in the second imaged spectrum. In one embodiment, the background color image does not record wavelengths that are within the fluorescence emission spectrum of the at least one fluorophore.

Both the first and the second imaged spectrum may overlap the visible spectrum.

The above configuration may be useful in a medical observation device, for example, a microscope or an endoscope. The microscope may be a laboratory microscope or a surgical microscope.

A medical observation device, such as a microscope or endoscope, may comprise the data processing device in any of the above embodiments. The medical observation device may further comprise a white-light color camera, which is configured to record the background image, and a fluorescence-light camera, which is configured to record the second image. The fluorescence-light camera may be a greyscale camera or a color camera. The term "color camera" comprises CCD, CMOS, multispectral and hyperspectral cameras, and all other type of cameras that record color images.

A method of operating a medical observation device may comprise the computer-implemented method in any of the embodiments described above and may further comprise the steps of recording a background color image of the object using the white-light color camera; and recoding a second image of the object using the fluorescence-light camera.

The claimed subject matter also relates to a computer-readable medium and a computer program comprising instructions to cause a computer to carry out the computer-implemented image processing in any of the above embodiments.

As used herein, the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus.

In the following, exemplarily embodiments are described with reference to the drawings. The combination of features that are shown in the embodiments is not to be considered as limiting. For example, features of the embodiments which have a technical effect as e.g. explained above that is not needed in a specific application may be omitted. Conversely, features described above that are not part of an embodiment described below may be added if the technical effect associated with this particular feature is needed in a specific application.

Throughout the description and the drawings, the same reference numerals are used for elements that correspond to each other with respect to function and/or structure.

FIG. 1 shows schematically a medical observation device 100. The medical observation device 100 may be a fluorescence microscope or a fluorescence endoscope, the difference between a microscope and an endoscope being primarily that, in an endoscope, an object 106 is viewed through optical fibers that are brought into vicinity of the object 106 to be investigated, e.g. by insertion into a body, whereas, in a microscope, an objective 174 is directed onto the object 106. Although the medical observation device of FIG. 1 is shown as a microscope, the following description also applies to an endoscope. The medical observation device 100 may be a medical observation device as e.g. used in surgery. The medical observation device 100 may also be a medical observation device used in a laboratory, such as a laboratory microscope. The object 106 to be investigated may consist of or comprise biological tissue 107 but may also comprise or consist of inorganic matter.

The object 106 may comprise one or more fluorophores 116, 118. The at least one fluorophore may be a fluorophore that is naturally contained in the object. For example, bone and blood contain fluorophores. The at least one fluorophore may also be added to the object 106, e.g. by injecting it into the biological tissue 107. Examples of fluorophores that may be added to the object 106 are ICG, fluorescein and/or 5-ALA. 5-ALA is synthesized in cells to pPIX.

The medical observation device 100 may be configured to record the fluorescence of the one or more fluorophores 116, 118. This means that the medical observation device 100 may be configured to view, record and preferably also excite the fluorescence of the one or more fluorophores 116, 118.

The medical observation device 100 may be a stereoscopic device as is exemplarily shown in FIG. 1. It may thus comprise two identical subassemblies 101L and 101R for each of the two stereoscopic channels. As the two subassemblies 101L, 101R are identical with respect to function and structure, the following description focuses on the right subassembly 101R, but applies identically to the left stereoscopic channel 101L.

The medical observation device 100 may alternatively be a monoscopic device. In this case, only one of the two subassemblies 101L, 101R may be present. For a monoscopic medical observation device 100, the following description therefore applies as well.

The medical observation device 100 may, in one embodiment, be used to generate one or more digital white-light color image 114. The digital white-light color image may in particular represent a reflectance image of the object 106 across the visible light range. The visible light range or visible spectrum comprises the wavelengths from about 310 nm to about 1100 nm, or from about 380 nm to 750 nm, or from about 450 nm to about 700 nm. The fluorescence spectrum or, if more than one fluorophore is used, the fluorescence spectra of the fluorophores 116, 118 is preferably omitted from the spectrum recorded in the digital white-light color image 114. This makes sure that only reflected light is contained in the digital white-light color image 114 if fluorescence is present. For example, if 5-ALA/pPIX is used as a fluorophore, the fluorescence spectrum from about 625 nm to about 650 nm may not be recorded in the digital white-light color image 114.

If light of specific wavelengths is used to excite fluorescence, the spectrum comprising or consisting of these wavelengths may also not be recorded or represented in the digital white-light color image 114. For example, if 5-ALA/pPIX is used as a fluorophore, fluorescence may be excited by illuminating the object 106 with wavelengths between about 380 nm to about 450 nm. For fluorescein and ICG and other fluorophores, different but known ranges for the excitation and emission spectra apply than for 5-ALA/pPIX.

When not recording the fluorescence-excitation spectrum and the fluorescence-emission spectrum, the digital white-light color image 114 represents the reflectance of the object 106, i.e. a white-light image of the object 106 as it would be seen by a human observer. In such a configuration, the digital white-light color image 114 may be regarded as a natural or true color image.

The digital imaging system 102 may further be used to generate one or more digital fluorescence-light images 112 of the object 106. A digital fluorescence-light image 112 may represent the fluorescence emission of the one or more fluorophores 116, 118. The digital fluorescence-light image 112 may be a greyscale or a color image.

The digital fluorescence-light image 112 preferably does not record any wavelengths outside the emission spectrum or the emission spectra of the one or more fluorophores. The digital fluorescence-light image 112 may also be a reflectance image of the object 106 or contain fluorescence-light and reflected light from the object.

The digital white-light color image 114 and the digital fluorescence-light image 112 may, in one embodiment, both be color images. They are recorded using at least three color bands or, equivalently, primary colors of a color space. For example, both the digital white-light color image 114 and the digital fluorescence-light image 112 may be recorded in a RGB color space using the three primary colors or color bands R, G, B. Alternatively, the digital white-light color image 114 and the digital fluorescence-light image 112 may each be recorded in a different color space, each of them may represent a multi-spectral or hyperspectral color image. The digital white-light color image 114 and the digital fluorescence image 112 need not be recorded in the same color space, although this is preferred.

The at least one digital white-light color image 114 and the at least one digital fluorescence-light image 112 contain pixels 150a, 150b respectively. In a color space such as an RGB color space, each color of a pixel 150a, 150b is represented by color space coordinates which form a triplet of three integer numbers. Each integer number indicates the intensity of one of the primary colors R, G, B. For example, the most intense red may be indicated by the triple {255, 0, 0}. The most intense green color may e.g. be indicated by {0, 255, 0}, and the most intense blue by e.g. {0, 0, 255}. Thus, RGB color space is a three-dimensional space, CMYK color space would be a four-dimensional space. A color can be considered as a point in color space having color space coordinates such as {0, 0, 255}. In a more general way, a multi-spectral or hyper spectral color space having n color bands would correspondingly result in an n-dimensional color space, and each color would be represented by an n-tuple of color space coordinates.

Examples of an RGB color space are RGB, sRGB, AdobeRGB, Adobe White Gamut RGB, REC. 2100, DCI-P3, Rec. 2020, Rec. 709, Rec. 601 and ACES.

The spectrum recorded and represented in the digital white-light color image 114, i.e. the first imaged spectrum, and the spectrum recorded in the digital fluorescence-light image 112, i.e. the second imaged spectrum, are preferably complementary to one another, i.e. do not overlap, except for unavoidable filter leakage. Preferably, they together represent the complete visible-light spectrum, or at least a major part of the visible light range. The first and/or the second image may also contain wavelengths outside the visible spectrum, such as NIR.

More specifically, the medical observation device 100 may comprise a digital imaging system 102 for generating the digital fluorescence-light image 112 and the digital white-light color image 114. The digital imaging system 102 may comprise a white-light color camera 110 and a fluorescence-light camera 111.

The white-light camera 110 is configured to record the digital white-light color image 114. In particular, the white-light color camera 110 may be configured to generate a stream of digital white-light color images 114 in the form of a digital video stream. The white-light color camera 110 is preferably configured to record a digital image across the entire visible spectrum in the wavelengths indicated above. The white-light color camera 110 may be a CCD, CMOS or multispectral or hyperspectral camera.

The fluorescence-light camera 111 is configured to record the digital fluorescence-light image 112. In particular, the fluorescence-light camera 111 may be configured to generate a stream of digital fluorescence-light images 112 in the form of a digital video stream. The fluorescence-light camera 111 may be configured to record the digital fluorescence-light image 112 only in the fluorescence spectrum or the fluorescence spectra of the at least one fluorophore 116, 118. The fluorescence-light camera 111 may be configured to record the digital fluorescence-light image 112 only in one or more narrow bands of light. These narrow bands should overlap the fluorescence spectrum or spectra of the one or more fluorophores 116, 118 of which fluorescence is to be recorded. Preferably, the fluorescence spectra of the fluorophore 116 and the second fluorophore 118 do not overlap so that the fluorescence-light camera 111 may record light in two separate fluorescence bands that are spaced from one another.

The fluorescence-light camera 111 may be a CCD, CMOS or multispectral or hyperspectral camera, or any other type of suitable camera. Preferably, the white-light color camera 110 and the fluorescence-light camera 111 are of the same type, although this is not necessary. As the fluorescence light has usually a very low intensity, the fluorescence-light camera 111 may have a higher integration time.

The respective fields of view 184 of the cameras 110, 111 are preferably aligned or even coinciding and coaxial. Thus, it is preferred that the cameras 110, 111 provide the identical field of view 184 with the identical perspective and focal length. This results in identical representations of the object 106 in the images 112, 114 generated by the different cameras 110, 111. Both cameras 110, 111 may use the same objective 174. In such a configuration, the images 112, 114 may be registered optically, which makes a registration by image processing unnecessary or much easier.

If a match of the perspectives and field of view cannot be generated optically, it may be generated by image processing by applying a matching or registering routine to the digital images 112, 114, as is explained further below. Applying a computer-implemented registering routine may even be advisable if the cameras 110, 111 have identical perspectives and fields of view.

It is preferred that the two cameras 110, 111 are operated synchronously. Specifically, the exposure times may be synchronized. Thus, the medical observation device 100 may be configured to generate the digital white-light color image 114 and the digital fluorescence-light image 112 at the same time.

Preferably, the gain of the two cameras 110, 111 is synchronized, i.e. adjusted in the two cameras 110, 111 at the same time. Moreover, the ratio of the gain applied in camera 110 to the gain applied in camera 111 may be constant, even if the gain is changed. The gamma correction and color adjustment or white balance may be switched off or kept constant.

Any of the above measures facilitates the comparison, joint processing and/or combining of the two images 112, 114

For separating the spectrum recorded in the digital white-light color image 114 from the spectrum recorded in the digital fluorescence-light image 112, i.e. for separating the reflectance spectrum from the fluorescence spectrum, the medical observation device 100 may comprise an optical color-separation assembly 176. The color-separation assembly 176 may comprise optical elements such as a beam splitter 192, which may be dichroic. The color separation assembly 176 may further or alternatively comprise an optical white-light filter 188 and/or an optical fluorescence-light filter 190.

The fluorescence-light filter 190 is preferably configured to transmit light in the fluorescence spectrum or spectra of the one or more fluorophores 116, 118 and to block light outside the fluorescence spectrum or spectra.

The fluorescence-light filter 190 may be configured as a band-pass filter comprising one or more passbands. Each passband should overlap the fluorescence emission spectrum of a respective fluorophore 116, 118 of which the fluorescence is to be recorded. As the fluorescence-light filter 190 is in the light path between the beam splitter 192 and the fluorescence-light camera 111, only the wavelengths in the passbands of the fluorescence-light filter 190 are transmitted to the fluorescence-light camera 111.

The white-light filter 188 is preferably configured to block light in the fluorescence spectrum or spectra of the one or more fluorophores 116, 118. The white-light filter 188 may also be configured to block light in the fluorescence-excitation spectrum.

The white-light filter 188 is preferably configured as a band-stop filter, of which the stop bands correspond to or at least contain the passbands of the fluorescence-light filter 190. The white-light filter 188 is located in the light path between the beam splitter 192 and the white-light camera 110. Thus, the white-light color camera 110 records only wavelengths that are outside the stop-bands of the white-light filter 188 and therefore also outside of the pass-bands of the fluorescence-light filter 190 of the fluorescence-light filter 190.

Any one of the white-light filter 188 and the fluorescence-light filter 190 may be a tunable filter.

If the beam splitter 192 is a dichroic beam splitter, at least one of the filters 188, 190 may be omitted as the optical spectral filtering in this case is already integrated in the dichroic beam splitter. The above description of the pass-bands and stop bands then should apply mutatis mutandis to the dichroic beam splitter 192.

Thus, the white-light color camera 110 records the digital white-light color image 114 in a first imaged spectrum, the reflectance spectrum, which is different from a second imaged spectrum, which is recorded as fluorescence spectrum by the fluorescence-light camera 111. The wavelengths that are contained in the first and the second imaged spectrum are determined by the filter settings of the color separation assembly 176.

The medical observation device 100 may further comprise an illumination assembly 178, which is configured to illuminate the object 106 preferably through the same objective 174 through which the imaging system 102 records the at least one digital image 112, 114. The illumination assembly 178 may be configured to selectively generate white-light, i.e. light that is evenly distributed across the entire visible spectrum, and fluorescence-excitation light, which contains light only in wavelengths that stimulate fluorescence of the at least one fluorophore 116, 118. The illumination light generated by the illumination assembly 178 may be fed into the objective 174 using an illumination beam splitter 180.

An illumination filter 179 may be provided depending on the fluorophore and its fluorescence-specific excitation spectrum. For example, if 5-ALA/pPIX is used as a fluorophore, the illumination filter 179 may have a transmission of 90% to 98% up to wavelengths of 425 nm, a transmission between 0.5% and 0.7% in wavelengths between 450 nm and 460 nm, a transmission of not more than 0.1% between 460 nm and 535 nm and of practically zero for wavelengths above 535 nm.

Instead of or in addition to the illumination filter 179, the illumination assembly 178 may comprise a tunable light source, comprising e.g. a multitude of differently colored LEDs or OLEDs.

The medical observation device 100 may further comprise a data processing device 170. The data processing device 170 may be a hardware module, such as a microprocessor, or a software module. The data processing device 170 may also be a combination of both a hardware module and a software module, for example by using software modules that are configured to be run on a specific processor, such as a vector processor, a floating point graphics processor, a parallel processor and/or on multiple processors. The data processing device 170 may be part of a general-purpose computer 186, such as a PC.

The data processing device 170 is configured to retrieve the digital white-light color image 114 and the digital fluorescence-light image 112. For example, the data processing device 170 may be configured to retrieve the digital white-light color image 114 and the digital fluorescence-light image 112 from a memory 194 and/or directly from the cameras 110, 111. The memory 194 may be part of the data processing device 170 or reside elsewhere in the medical observation device 100.

The data processing device 170 is further configured to compute a digital output color image 160 from the digital white-light color image 114 and the digital fluorescence-light image 112. The digital output color image 160 is a color image which is represented in a color space, which may be different from the color space of any of the digital white-light color image 114 and the digital fluorescence-light image 112. Preferably, however, the color space of the digital output color image 160 is the same color space as that of the digital white-light color image 114 and the digital fluorescence-light image 112. For converting the coordinates from one color space to another, standardized functions exist, or may be determined experimentally or analytically. In case of fluorescence, the fluorescence intensity, i.e. brightness may be used for the luminance. If the fluorescence-light image is a greyscale image, the intensity or luminance value is directly recorded in the fluorescence-light image. If the fluorescence-light image is a color image, the intensity or luminance may be computed using the functions appropriate for this color space.

The data processing device 170 is preferably configured to generate a digital output color image 160 from the digital fluorescence-light image 112 and the digital white-light color image 114.

The digital white-light color image 114 may, in one embodiment, serve as a background color image on which the fluorescence-light image 112 is overlaid as a second image. In another embodiment, the digital fluorescence-light color image 112 may be used as the background image whereas the second pixel 150b corresponds to pixel from the digital white-light color image 114.

The data processing device 170 may be configured to combine the second image 112 and the background color image 114 to generate the digital output color image 160 using a color conversion function 140. The generation of the output color image 160 may take place on a pixel-by-pixel base, where a first pixel 150a of the background color image 114 is combined with a second pixel 150b from the second image 112 using the color conversion function 140 to form an output pixel 150c.

The first and second pixels 150a, 150b are preferably corresponding pixels. Thus, in registered images 112, 114, the first and second pixels 150a, 150b may be located at the same location within the respective images 112, 114.

The number of pixels in the images 112, 114 do not necessarily need to be the same. For example, a pixel in one image 112, 114 with higher resolution may correspond to a plurality of pixels in the other image 114, 122 with lower resolution. Alternatively, two pixels which are located in the same location within the same pattern that has been identified by a pattern recognition algorithm in both images 112, 114 may be regarded as corresponding pixels.

In a surgical context, the background color image 114 may represent the background anatomy image over which fluorescence information is overlaid. If the fluorescence recorded in the second image 112 is to be represented with a predetermined overlay color 152, e.g. a pseudocolor, the color of the output pixel 150c may be computed using the color of the first pixel 150b, the luminance of the second pixel 150b, and the predetermined overlay color.

The data processing device 170 may be configured to output the digital output color image 160 to any kind of peripheral device. Outputting in this context comprises sending of and/or allowing access to the digital output color image 160, e.g. by allowing access to a memory, such as memory 194, where the digital output color image 160 may be stored, or output on an output interface 172 of the medical observation device 100.

The digital output color image 160 may be displayed on the display 132 which is integral to the medical observation device 100. For example, the display 132 may be integrated in an ocular or eyepiece 104 of the medical observation device 100. The display 132 may also display a graphical user interface for operating the medical observation device 100.

The overlay color 152 may be stored in the data processing device 170 and/or the computer 186 and be changed according to user preferences.

The medical observation device 100 may comprise a direct optical path 134 from the object 106 through the objective 174 to the eyepiece 104. In such a case, the display may be a translucent display 132 located in the direct optical path 134 or the display may be projected into the direct optical path 134. A beam splitter 136 may be provided to split the light between the optical eyepiece 104 and the digital imaging system 102. In one embodiment, up to 80% of the light may be directed to the eyepiece 104.

in another embodiment, the medical observation device 100 does not necessarily have a direct optical path 134 but may only display images using the integral display 132. As a further alternative, the medical observation device 100 does not need to have any integrated display at all.

The medical observation device 100 may comprise an output interface 172 to which one or more (external) displays 182 and/or any type of uni- or bidirectional wired or wireless data connection may be connected. For this, the output interface 172 may comprise standardized connectors and data transmission protocols, such as WLAN, TCP/IP, Ethernet, USB, HDMI, DVI, DisplayPort, Bluetooth and/or others. An external display may be a monitor, 3D goggles, oculars and the like. Any combination of external displays may be connected to the output interface 172. Any of the displays 182 may display a graphical user interface for operating the medical observation device 100.

The computer 186 or the data processing device 170 may be connected to the digital imaging system 102 using one or more data transmission lines 196. A data transmission line may be wired or wireless, or partly wired and partly wireless. The computer 186 and/or the data processing device 170 may not be bodily integrated in the medical observation device 100 but be physically located remote from the digital imaging system 102. For this, the digital imaging system 102 and the computer 186 and/or the data processing device 170 may be connected to a network, such as a LAN, a WLAN or a WAN, to which also at least one display 182 may be connected. The network connectivity may be provided by the output interface 172.

According to a modification, the medical observation device 100 may be stereoscopic but comprise only two cameras, one for each stereoscopic channel. In one stereoscopic channel, the fluorescence-light camera 111 is used and configured to selectively also record white-light reflectance, whereas in the other stereoscopic channel, the white-light color camera 110 is used. Such an arrangement provides a stereoscopic white-light color image if no fluorescence is used and a monoscopic white-light color image and a monoscopic fluorescence-light image if fluorescence is used. The description above and below applies equally to this configuration.

According to another configuration, each stereoscopic channel may comprise more than two cameras.

Figure 3A:
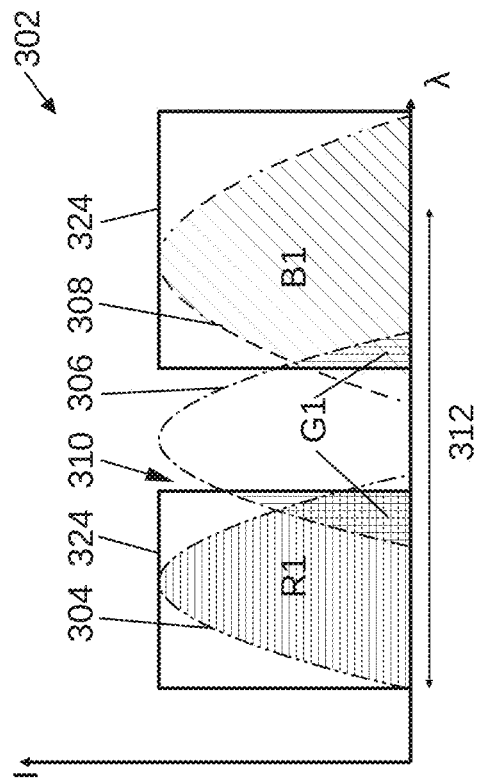
FIGS. 3A and 3B show schematic representations of examples of the imaged spectra in the first image and the second image, respectively, according to some embodiments.

In FIG. 3A, a quantitative example of the first imaged spectrum 302 is shown as it is recorded by the digital white-light camera 110 and/or represented in the digital white-light color image 114, respectively. The intensity I across the wavelengths/colors 2 is shown as normalized. The first imaged spectrum 302 preferably extends at least across the visible spectrum 312.

Just by way of example, the color space in which the first imaged spectrum 302 is recorded, is an RGB color space having three primary colors or color bands 304, 306 and 308. One primary color 304 is blue, another primary color 306 is green and a third primary color 308 is red. The sensitivities of the sensors of the white-light color camera 110 in the different primary colors 304, 306, 308 may be tuned to result in a sensitivity across the visible spectrum 312 which is as constant as possible.

If a color space other than RGB is used, the quantity, locations and/or widths of the color bands may be different.

The first imaged spectrum 302 preferably does not include the fluorescence-excitation light and the fluorescence emission spectrum of the at least one fluorophore 116, 118. Thus, the first imaged spectrum 302 may include at least one stop band 310 which coincides with the fluorescence emission of the at least one fluorophore of which fluorescence is to be also recorded by the fluorescence-light camera 111. The stop band 310 is e.g. created by the white-light filter 188. The number, width, and/or location of stop bands 310 depend on the number and types of fluorophores to be observed in the object 106.

Figure 3B:
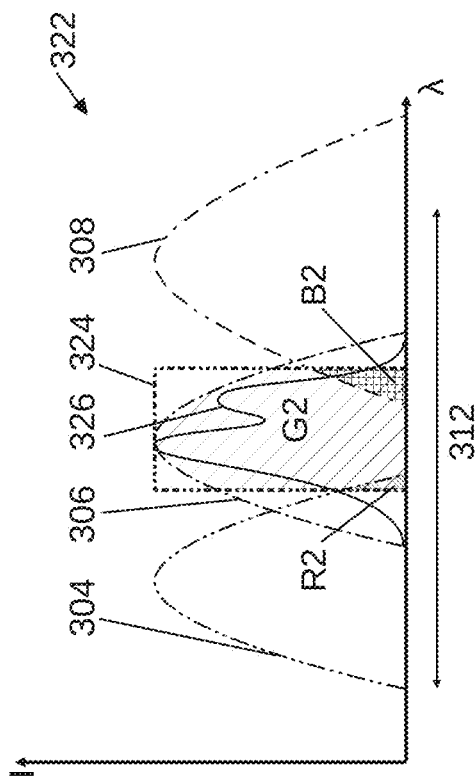

The second imaged spectrum 322 is shown in FIG. 3B as it is recorded by the fluorescence-light camera 111 and/or represented in the digital fluorescence-light color image 112, respectively. Just by way of example, the color space in which the second imaged spectrum 322 is recorded is also an RGB color space. The sensitivities of the sensors of the fluorescence-light camera 111 in the different primary colors 304, 306, 308 are tuned to result in a sensitivity across the visible spectrum 312 which is as constant as possible.

The spectra 302, 322 do not need to be recorded in the same color space, although this is preferred.

The second imaged spectrum 322 may comprise one or more passbands 324. The number, location and/or width of the passbands depends on the number and types of fluorophores used. The at least one passband 324 preferably corresponds to the at least one stop band 310. The at least one passband is e.g. generated by the fluorescence-light filter 190.

The first imaged spectrum 302 and the second imaged spectrum 322 are complementary to one another. They preferably complete each other to cover the entire, more than or most of the visible spectrum 312.

Each passband 324 of the second imaged spectrum 322 preferably overlaps the fluorescence-emission spectrum 326 of a fluorophore 116, 118, of which fluorescence is to be recorded, and overlap one or more primary colors 304, 306, 308 of the color spectrum. For example, the fluorescence-emission spectrum 326 of a fluorophore 116 may overlap all three primary colors 304, 306, 308.

Figure 2:
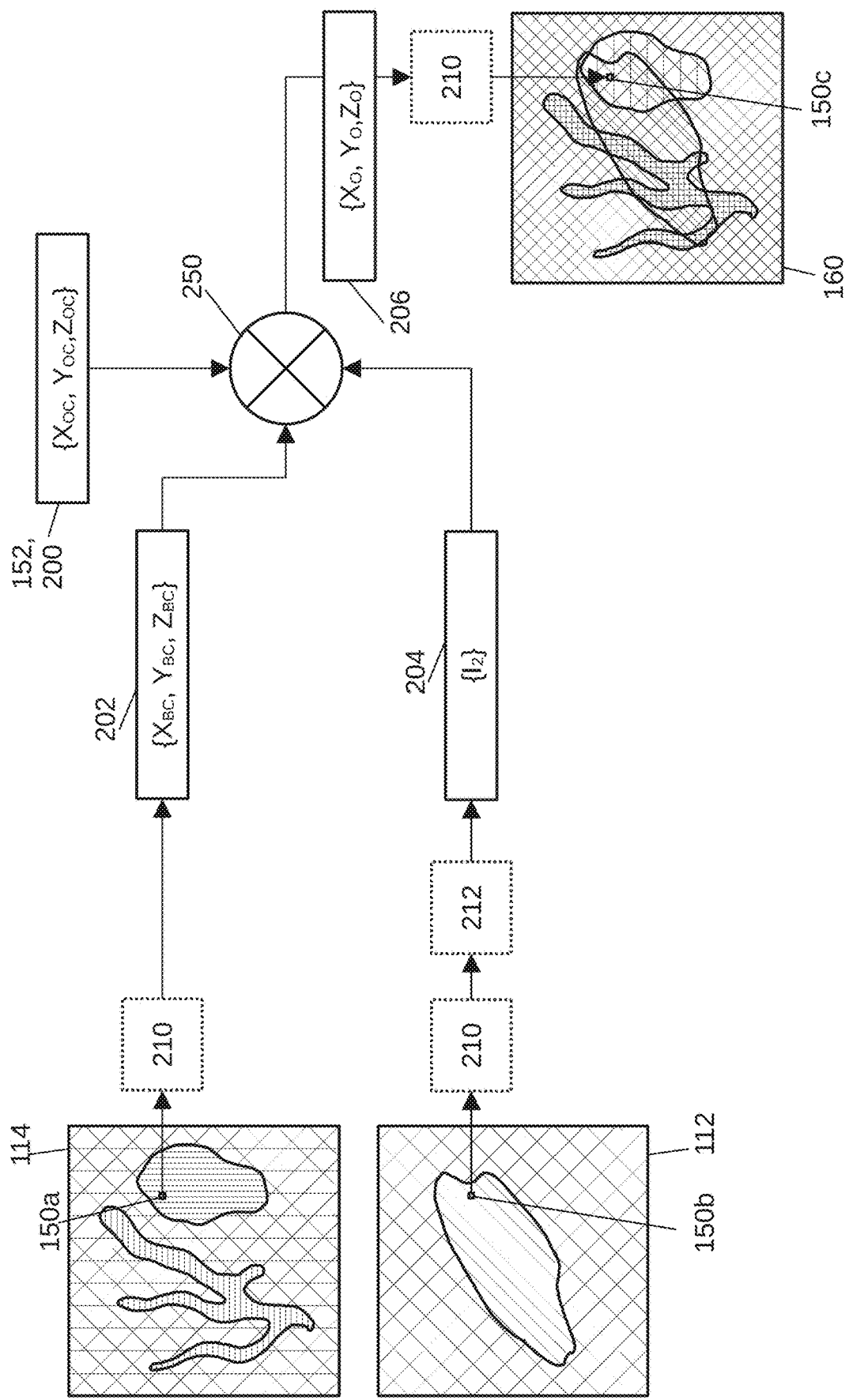
FIG. 2 shows a schematic representation of an example of a combination of a first image, a second image and an overlay color to generate an output image according to some embodiments.

Next, the process of combining the images 112, 114 using the overlay color 152 is explained with reference to FIG. 2. The data processing device 170 is configured to carry out any step of this process.

In order to obtain a color mix from the background color of the first pixel 150a and the overlay color 152 which corresponds most closely to the human color perception, color mixing is performed in a uniform color space such as the CIELAB color space, CIELUV color space, HSLuv color space IPT color space, OKLab color space, and a tristimulus color space.

If the digital white-light color image 114, which forms the background color image in this example, is recorded in a non-uniform color space, such as a RGB color space, it is converted at step 210 into the uniform color space. Thus, at step 210, color-space conversion into a uniform color space is performed for the first pixel 150a. The background color coordinates 202 of the first pixel 150a in the uniform color space are {XBC, YBC, ZBC}, where X, Y, Z are e.g. in CIELAB color space the coordinates L, a, b, and in CIELUV color space, the coordinates L, U. V.

The same is done for the fluorescence-light image 112 as the second image if it is a color image which has been recorded in a non-uniform color space, e.g. a RGB color space: At step 210 color-space conversion is performed for the second pixel 150b. The color space coordinates of the first and the second pixel 150a, 150b should be converted into the same uniform color space. If the fluorescence-light image is a greyscale image, a color space transformation is not necessary.

If, again, the fluorescence-light image is a color image, the luminance value at the second pixel 150b is computed. It is to be noted that luminance computation 212 may also be performed before color-space conversion 210. Thus a light intensity value I2 is obtained for the second pixel 150b.

The overlay color coordinates 200 of the overlay color 152 are {XOC, YOC, ZOC} in the uniform color space. Of course, if the overlay color coordinates are not in the uniform color space of the first and the second pixel 150a, 150b, they may be transformed to the uniform color space.

A color conversion using the overlay color coordinates 200, the light intensity value 204 and the background color coordinates 202 is performed at step 250, resulting in output color coordinates 206, i.e. a tuple {XO, YO, ZO} for the output pixel 150c. The output pixel 150c is located preferably at the same position in the output color image 160 as the first and second pixels 150a, 150b in their respective images 112, 114.

The output color coordinates 206 may then be converted into a color space which is more suited for an output device such as a display 132, 182, e.g. again a RG color space. Thus, again, a color space transformation 210 is performed.

Figure 4:
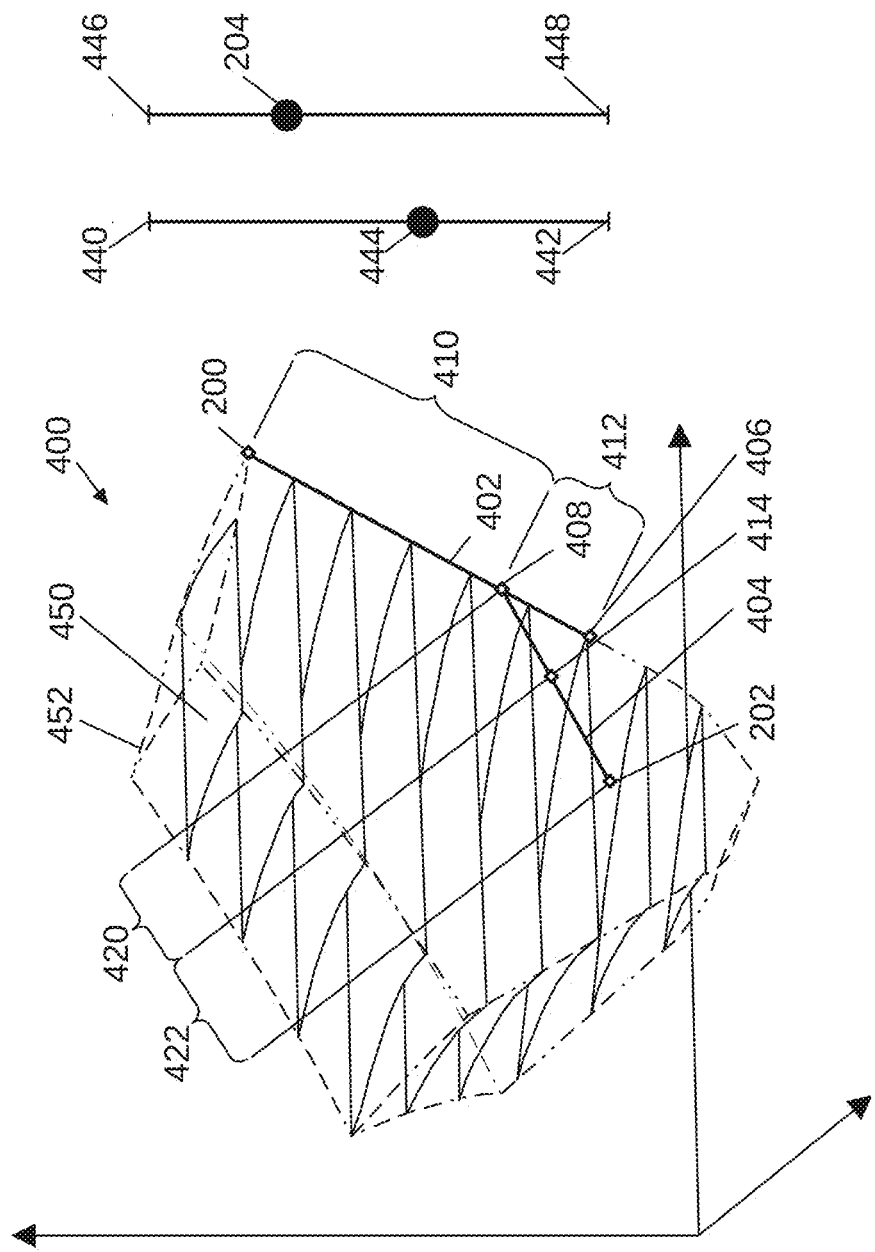
FIG. 4 shows a schematic representation of mixing a color of the first image with an overlay color depending on a light intensity in a second image, according to some embodiments.

With reference to FIG. 4, the color conversion 250 that is done by the color conversion function 140 is explained in closer detail. FIG. 4 shows just a uniform color space 400, in particular, just by way of example, a CIELAB color space.

First, a luminance line 402 is computed. The luminance line 402 starts at the overlay color space coordinates 200 and extends continuously along points where only luminance changes, but the chroma is constant. In a uniform color space, where luminance is a coordinate, e.g. CIELAB, the luminance line 402 extends along the luminance coordinate. In another uniform color space, the luminance line 402 may not be a straight line.

An end point 406 of the luminance line 402 is determined by e.g. a predetermined value of the luminance in relation to the luminance of the overlay color space coordinates 200. For example, the end point 406 may be located where, at the same chroma, luminance is at 20 percent of the luminance of the overlay color space coordinates 200. Of course any other predetermined ratio may be used.

If, using the a predetermined luminance ratio, the end point 406 is located outside of the gamut 452 of a predetermined display device, such as one of the displays 132, 182, the end point 406 is positioned at the intersection of the luminance line 402 with the limit of the gamut 452.

Next, a first point 408 is computed on the luminance line 402. The position of the first point 408 along the luminance line 402 corresponds to the position of the luminance 444 of the background color 202 within the range of possible luminance values in the uniform color space 400 or within the gamut 452 for the chroma of the background color. This range extends between a predetermined maximum luminance value 440 and a predetermined minimum luminance value 442, including these values. The maximum and/or minimum luminance values 440, 444 may depend on the chroma of the background color.

More specifically, the ratio of the distance 410 from the first point 408 to the overlay color space coordinates 200 and the distance 412 from the first point 408 to the end point 406 is the same as the ratio of the difference between the maximum luminance value 440 and the luminance of the background color coordinates {XBC, YBC, ZBC} and the difference between the minimum luminance value 442 and the luminance value of the background color coordinates.

If, for example, the maximum luminance value 440 for the chroma of the background color is 251 in the gamut 452 and the minimum luminance value 442 for the chroma of the background color is 3 in the gamut 452, and the luminance of the background color 202 is 134, then the ratio of the length 410 to the length 412 is (251−134)/(134−3). The brighter the background color, the closer the first point 408 is to the overlay color coordinates 200.

Once the first point 408 is determined, an overlay color line 404 is computed. The overlay color line 404 extends straight in any uniform color space 400 from the background color coordinates 202 to the first point 408. The output color coordinates 206 are determined as the coordinates of a second point 414 which is located on the overlay color line 404.

The location of the second point 414 depends on the light intensity value 204 of the second pixel 150b. The distance between the second point 414 and the background color coordinates 202 corresponds to the relative intensity of the light intensity value 204 in relation to the maximum rage of intensities. The higher the light intensity value 204, the closer the second point 414 is to the luminance line 404. The light intensity value 204 ranges from a maximum light intensity value 446 to a minimum light intensity value 448, wherein the maximum and minimum values are included in the range.

In particular, the ratio of the difference between the maximum light intensity value 446 and the light intensity value 204 and the difference between the light intensity value 204 and the minimum light intensity value 448 corresponds to the ratio of a length 420 of the overlay color line 404 between the second point 414 and the first point 408 and the length 422 of the overlay color line 404 between the background color coordinates 202 and the second point 414.

If, for example, the maximum light intensity value 446 of the first pixel 150a is 1024, the minimum light intensity value 448 of the first pixel is 0 and the light intensity value of the second pixel 150b is 347, then the ratio of the length 420 and the length 422 is (1024−347)/(347−0).

The maximum light intensity value and the minimum light intensity value may be determined by the color space or the gamut of the predetermined display device or, alternatively by the range of the camera recording the second image. The maximum and/or minimum intensity value 446, 448 may represent a neutral color, for example, the minimum light intensity may correspond to black and/or the maximum light intensity may correspond to white in the uniform color space and/or gamut.

The minimum and maximum luminance values and/or the maximum and minimum intensity values may be stored in memory 194.

Although a medical observation device 100 is described in the preceding description, the mixing method and the data processing device 170 are not limited to these devices. For example, instead of representing fluorescence, the second image may represent reflectance, IR light, microwaves or other electromagnetic waves outside the visible spectrum. Further, other image sources such as X-ray or MR images may be used as the background or second image.

Figure 5:
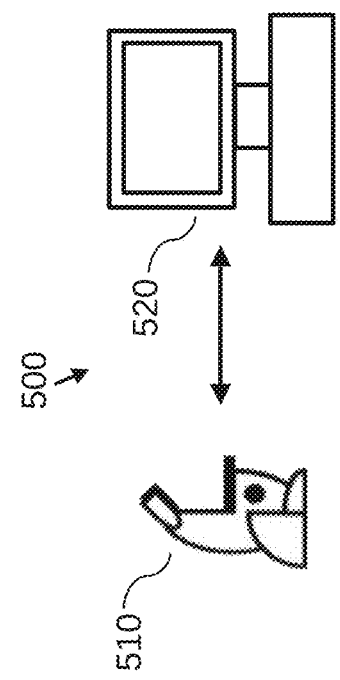
FIG. 5 shows a schematic representation of a system according to some embodiments.

FIG. 5 shows a schematic illustration of a system 500 configured to perform a method described herein. The system 500 comprises a microscope 510 and a computer system 520. The microscope 510 is configured to take images and is connected to the computer system 520. The computer system 520 is configured to execute at least a part of a method described herein. The computer system 520 may be configured to execute a machine learning algorithm. The computer system 520 and microscope 510 may be separate entities but can also be integrated together in one common housing. The computer system 520 may be part of a central processing system of the microscope 510 and/or the computer system 520 may be part of a subcomponent of the microscope 510, such as a sensor, an actor, a camera or an illumination unit, etc. of the microscope 510.

The computer system 520 may be a local computer device (e.g. personal computer, laptop, tablet computer or mobile phone) with one or more processors and one or more storage devices or may be a distributed computer system (e.g. a cloud computing system with one or more processors and one or more storage devices distributed at various locations, for example, at a local client and/or one or more remote server farms and/or data centers). The computer system 520 may comprise any circuit or combination of circuits. In one embodiment, the computer system 520 may include one or more processors which can be of any type. As used herein, processor may mean any type of computational circuit, such as but not limited to a microprocessor, a microcontroller, a complex instruction set computing (CISC) microprocessor, a reduced instruction set computing (RISC) microprocessor, a very long instruction word (VLIW) microprocessor, a graphics processor, a digital signal processor (DSP), multiple core processor, a field programmable gate array (FPGA), for example, of a microscope or a microscope component (e.g. camera) or any other type of processor or processing circuit. Other types of circuits that may be included in the computer system 520 may be a custom circuit, an application-specific integrated circuit (ASIC), or the like, such as, for example, one or more circuits (such as a communication circuit) for use in wireless devices like mobile telephones, tablet computers, laptop computers, two-way radios, and similar electronic systems. The computer system 520 may include one or more storage devices, which may include one or more memory elements suitable to the particular application, such as a main memory in the form of random access memory (RAM), one or more hard drives, and/or one or more drives that handle removable media such as compact disks (CD), flash memory cards, digital video disk (DVD), and the like. The computer system 520 may also include a display device, one or more speakers, and a keyboard and/or controller, which can include a mouse, trackball, touch screen, voice-recognition device, or any other device that permits a system user to input information into and receive information from the computer system 520.

Some or all of the method steps may be executed by (or using) a hardware apparatus, for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

REFERENCE NUMERALS 100 medical observation device
101L stereoscopic subassembly for the left channel
101R stereoscopic subassembly for the right channel
102 digital imaging system
104 eyepiece
106 object to be investigated
107 biological tissue
110 white-light color camera
111 fluorescence-light camera (color or greyscale)
112 fluorescence-light/second image (color or greyscale)
114 white-light/background color image
116 fluorophore
118 second fluorophore
132 integral/internal image display device
134 direct optical path
136 beam splitter
140 color conversion function
150a first pixel in background color-image
150b second pixel in second image
150c output pixel in output color-image
152 overlay color
160 output color-image
170 data processing device
172 output interface
174 objective
176 color-separation assembly
178 illumination assembly
179 illumination filter
180 illumination beam splitter
182 image display device
184 field of view
186 computer
188 white-light filter
190 fluorescence-light filter
192 dichroic beam splitter
194 memory
196 data transmission line
200 overlay color coordinates, {XOC, YOC, ZOC}, overlay color
202 background color coordinates, {XBC, YBC, ZBC}, background color
204 light intensity value, I2
206 output color coordinates of output color, {XO, YO, ZO}, output color
210 color space transformation
212 luminance computation
250 color conversion
302 first imaged spectrum
304, 306, 308 color space coordinate
310 stop band 312 visible spectrum or light range
322 second imaged spectrum
324 passband
326 fluorescence-emission spectrum of a fluorophore
400 uniform color space
402 luminance line
404 overlay color line
406 end point of luminance line
408 first point, on the luminance line
410 length between the first point and the overlay color coordinates
412 length between the end point and the first point
414 second point, on the overlay color line
420 length between the second point and the first point
422 length between the background color coordinates and the second point
440 maximum luminance value
442 minimum luminance value
444 luminance of background color
446 maximum light intensity value
448 minimum light intensity value
450 plane of constant luminance
452 gamut
500 system
510 microscope
520 computer system
I intensity
I2 light intensity value
R, G, B primary colors of RGB color space
XBC, YBC, ZBC color space coordinates of color of first pixel in uniform color space
XOC, YOC, ZOC color space coordinates of overlay color in uniform color space
XO, YO, ZO color space coordinates of color of output pixel in uniform color space
λ wavelength

The invention claimed is:

1. A data processing device for computing an output color of an output pixel in an output color image by mixing a background color of a first pixel in a background color image with an overlay color depending on a light intensity value of a second pixel in a second image, wherein the data processing device is configured to perform operations comprising:

retrieve background color coordinates of the background color in a uniform color space, the background color having a predetermined maximum luminance value and a predetermined minimum luminance value in the uniform color space;

retrieve overlay color coordinates of the overlay color in the uniform color space;

retrieve the light intensity value, the light intensity value being in a range extending from and including a predetermined minimum light intensity value to and including a predetermined maximum light intensity value;

compute a luminance line in the uniform color space, the luminance line extending from the overlay color coordinates to an end point, a luminance at the end point being lower than a luminance at the overlay color coordinates, the luminance line extending along points having a chroma of the overlay color coordinates;

determine a first point on the luminance line, wherein a ratio of a difference between the predetermined maximum luminance value and a luminance of the background color coordinates and a difference between the luminance of the background color coordinates and the predetermined minimum luminance value corresponds to a ratio of a length of the luminance line between the first point and the overlay color coordinates and a length of the luminance line between the end point and the first point;

compute an overlay color line that extends straight from the background color coordinates to the first point;

determine a second point on the overlay color line, wherein a ratio of a difference between the predetermined maximum light intensity value and the light intensity value and a difference between the light intensity value and the predetermined minimum light intensity value corresponds to a ratio of a length of the overlay color line between the second point and the first point and a length of the overlay color line between the background color coordinates and the second point; and output color coordinates of the second point in the uniform color space as the output color of the output pixel.

2. The data processing device according to claim 1, wherein the end point of the luminance line is located within a gamut of a predetermined display device.

3. The data processing device according to claim 1, wherein the luminance line is a straight line in the uniform color space.

4. The data processing device according to claim 1 wherein the data processing device is configured to transform the overlay color coordinates from a non-uniform color space to the uniform color space before retrieving the overlay color coordinates.

5. The data processing device according to claim 1, wherein the data processing device is configured to transform the background color coordinates from a non-uniform color space to the uniform color space before retrieving the background color coordinates.

6. The data processing device according to claim 1, wherein the data processing device is configured to transform the color coordinates of the second point from the uniform color space to a non-uniform color space before outputting the color coordinates of the second point.

7. The data processing device according to claim 1, wherein the data processing device is configured to:

retrieve the first pixel from the background color image, the first pixel comprising the background color coordinates;

retrieve the second pixel from the second image, the second pixel comprising the light intensity value.

8. The data processing device according to claim 1, where the second image is one of a greyscale image and a color image.

9. The data processing device according to claim 1, wherein the data processing device is configured to:

retrieve the background color image, which is recorded in a first imaged spectrum, the background color image comprising a plurality of first pixels;

retrieve the second image, which is recorded in a second imaged spectrum, the second image comprising a plurality of second pixels;

wherein the second imaged spectrum overlaps with a fluorescence emission spectrum of at least one fluorophore, wherein the second imaged spectrum is different from the first imaged spectrum, and wherein both the first imaged spectrum and the second imaged spectrum overlap with a visible spectrum.

10. The data processing device according to claim 9, wherein the ratio of the luminance at the overlay color coordinates and the luminance at the end point of the luminance line is independent of the background color coordinates of the first pixels and/or the light intensity value of the second pixels.

11. The data processing device according to claim 1, wherein the background color image and the second image are registered.

12. A computer-implemented method for computing an output color of an output pixel in an output color image by mixing a background color of a first pixel in a background color image with an overlay color depending on a light intensity value of a second pixel in a second image, the computer-implemented method comprising:
  retrieving background color coordinates of the background color in a uniform color space, the uniform color space having a predetermined maximum luminance value and a predetermined minimum luminance value;
  retrieving overlay color coordinates of the overlay color in the uniform color space;
  retrieving the light intensity value, the light intensity value being in a range extending from and including a minimum light intensity value to and including a maximum light intensity value;
  computing a luminance line in the uniform color space, the luminance line extending from the overlay color coordinates to an end point, a luminance at the end point being lower than a luminance at the overlay color coordinates, the luminance line extending along points having a chroma of the overlay color coordinates;
  determining a first point on the luminance line, wherein a ratio of
    a difference between the predetermined maximum luminance value and the luminance of the background color coordinates and
    a difference between the luminance of the background color coordinates and the predetermined minimum luminance value
  corresponds to a ratio of
    a length of the luminance line between the first point and the overlay color coordinates and
    a length of the luminance line between the end point and the first point;
  computing an overlay color line that extends straight from the background color coordinates to the first point;
  determining a second point on the overlay color line, wherein
  a ratio of
    a difference between the maximum light intensity value and the light intensity value and
    a difference between the light intensity value and the minimum light intensity value
  corresponds to a ratio of
    a length of the overlay color line between the second point and the first point and
    a length of the overlay color line between the background color coordinates and the second point; and
  outputting color coordinates of the second point in the uniform color space as the output color.

13. A non-transitory computer-readable medium having a computer program stored thereon, the computer program, when executed by a computer, causing performance of the method claim 12.

14. A medical observation device, comprising:
  a white-light color camera configured to record a background color image;
  a fluorescence-light camera configured to record a second image; and
  the data processing device according to claim 1.

15. An operating method of a medical observation device, the operating method comprising the computer-implemented method of claim 12 and further comprising
  recording the background color image of the object using a white-light color camera; and
  recording the second image of the object using a fluorescence-light camera.

* * * * *